United States Patent
Ramstedt et al.

(10) Patent No.: US 9,044,470 B2
(45) Date of Patent: *Jun. 2, 2015

(54) IMINOSUGARS AND METHODS OF TREATING VIRAL DISEASES

(71) Applicants: United Therapeutics Corporation, Silver Spring, MD (US); The Chancellor, Masters and Scholars of the University of Oxford, Oxford (GB)

(72) Inventors: Urban Ramstedt, Silver Spring, MD (US); Brennan Klose, Silver Spring, MD (US); Nicole Zitzmann, Oxford (GB); Raymond A. Dwek, Oxford (GB); Terry D. Butters, Oxford (GB)

(73) Assignees: United Therapeutics Corporation, Silver Spring, MD (US); The Chancellor, Masters and Scholars of The University of Oxford, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/870,341

(22) Filed: Apr. 25, 2013

(65) Prior Publication Data

US 2013/0237567 A1    Sep. 12, 2013

Related U.S. Application Data

(63) Continuation of application No. 12/656,992, filed on Feb. 22, 2010, now Pat. No. 8,450,345.

(60) Provisional application No. 61/202,367, filed on Feb. 23, 2009, provisional application No. 61/272,255, filed on Sep. 4, 2009.

(51) Int. Cl.
*A61K 31/445*    (2006.01)
*A61P 31/20*    (2006.01)
*A61K 31/665*    (2006.01)

(52) U.S. Cl.
CPC ............ *A61K 31/445* (2013.01); *A61K 31/665* (2013.01)

(58) Field of Classification Search
CPC .......................... A61K 31/445; A61K 31/665
USPC ......... 514/315, 317, 151, 330, 326, 327, 408, 514/423, 424, 426, 422; 542/216
See application file for complete search history.

(56) References Cited

U.S. PATENT DOCUMENTS

| 4,182,767 A | 1/1980 | Murai et al. |
| 4,246,345 A | 1/1981 | Kinast et al. |

(Continued)

FOREIGN PATENT DOCUMENTS

| EP | 1 061 922 B1 | 12/2000 |
| EP | 1 137 416 B1 | 10/2001 |

(Continued)

OTHER PUBLICATIONS

Rawlings et al., "Synthesis and Biological Characterisation of Novel N-Alkyl-Deoxynojirimycin α-Glucosidase Inhibitors," ChemBioChem, Apr. 17, 2009, 10:1101-1105.

(Continued)

*Primary Examiner* — Savitha Rao
(74) *Attorney, Agent, or Firm* — Foley & Lardner LLP

(57) ABSTRACT

Provided are methods of treating or preventing viral infections caused by or associated with a Dengue virus using iminosugars.

6 Claims, 14 Drawing Sheets

(56) References Cited

U.S. PATENT DOCUMENTS

| | | | |
|---|---|---|---|
| 4,260,622 | A | 4/1981 | Junge et al. |
| 4,266,025 | A | 5/1981 | Kinast et al. |
| 4,278,683 | A | 7/1981 | Stoltefuss et al. |
| 4,405,714 | A | 9/1983 | Kinast et al. |
| 4,639,436 | A | 1/1987 | Junge et al. |
| 4,806,650 | A | 2/1989 | Schroeder et al. |
| 4,994,572 | A | 2/1991 | Fleet |
| 5,030,638 | A | 7/1991 | Partis et al. |
| 5,043,273 | A | 8/1991 | Scudder et al. |
| 5,103,008 | A | 4/1992 | Scudder et al. |
| 5,200,523 | A | 4/1993 | Fleet |
| 5,472,969 | A | 12/1995 | Platt et al. |
| 5,550,243 | A | 8/1996 | Khanna et al. |
| 5,622,972 | A | 4/1997 | Bryant et al. |
| 6,465,487 | B1 | 10/2002 | Block et al. |
| 6,495,570 | B2 | 12/2002 | Jacob et al. |
| 6,545,021 | B1 | 4/2003 | Mueller et al. |
| 6,610,703 | B1 | 8/2003 | Jacob et al. |
| 6,689,759 | B1 | 2/2004 | Jacob et al. |
| 6,696,059 | B2 | 2/2004 | Jacob et al. |
| 6,809,803 | B1 | 10/2004 | O'Brien et al. |
| 7,256,005 | B2 | 8/2007 | Zitzmann et al. |
| 7,446,098 | B2 | 11/2008 | Fan |
| 8,426,445 | B2 | 4/2013 | Pollock et al. |
| 2004/0110795 | A1 | 6/2004 | Zitzmann et al. |
| 2005/0256168 | A1 | 11/2005 | Block et al. |
| 2006/0074107 | A1 | 4/2006 | Butters et al. |
| 2006/0153829 | A1 | 7/2006 | Fan |
| 2006/0251680 | A1 | 11/2006 | Dwek et al. |
| 2006/0264467 | A1 | 11/2006 | Mugrage et al. |
| 2007/0178081 | A1 | 8/2007 | Fan |
| 2007/0244184 | A1 | 10/2007 | Pinto et al. |
| 2007/0275998 | A1 | 11/2007 | Butters et al. |
| 2008/0131398 | A1 | 6/2008 | Jeffs et al. |
| 2008/0138351 | A1 | 6/2008 | Dwek et al. |
| 2009/0042268 | A1 | 2/2009 | Gu et al. |
| 2009/0186847 | A1 | 7/2009 | Stein et al. |
| 2009/0186862 | A1 | 7/2009 | Aerts et al. |
| 2009/0252785 | A1 | 10/2009 | Pollock et al. |
| 2010/0004156 | A1 | 1/2010 | Kaushal et al. |
| 2010/0068141 | A1 | 3/2010 | Kaushal et al. |
| 2010/0222384 | A1 | 9/2010 | Ramstedt et al. |
| 2010/0266678 | A1 | 10/2010 | Pollock et al. |
| 2010/0317696 | A1 | 12/2010 | Ramstedt et al. |
| 2011/0065752 | A1 | 3/2011 | Ramstedt et al. |
| 2011/0065753 | A1 | 3/2011 | Ramstedt et al. |
| 2011/0065754 | A1 | 3/2011 | Ramstedt et al. |

FOREIGN PATENT DOCUMENTS

| | | |
|---|---|---|
| EP | 1 714 676 A2 | 10/2006 |
| WO | WO 00/33843 A1 | 6/2000 |
| WO | WO 01/07078 A1 | 2/2001 |
| WO | WO 2004/074450 A2 | 9/2004 |
| WO | WO 2006/077427 A2 | 7/2006 |
| WO | WO 2006/096769 A2 | 9/2006 |
| WO | WO 2006/124676 A1 | 11/2006 |
| WO | WO 2007/014327 A2 | 2/2007 |
| WO | WO 2007/123403 A1 | 11/2007 |
| WO | WO 2008/068548 A1 | 6/2008 |
| WO | WO 2008/088581 A2 | 7/2008 |

OTHER PUBLICATIONS

U.S. Appl. No. 61/282,507, filed Feb. 22, 2010, Ramstedt et al.
U.S. Appl. No. 61/272,252, filed Sep. 4, 2009, Ramstedt et al.
U.S. Appl. No. 61/272,253, filed Sep. 4, 2009, Ramstedt et al.
U.S. Appl. No. 61/272,254, filed Sep. 4, 2009, Ramstedt et al.
U.S. Appl. No. 61/282,508, filed Feb. 22, 2010, Ramstedt et al.
U.S. Appl. No. 61/353,935, filed Jun. 11, 2010, Ramstedt et al.
U.S. Appl. No. 12/656,993, filed Feb. 22, 2010, Ramstedt et al.
U.S. Appl. No. 12/732,630, filed Mar. 26, 2010, Ramstedt et al.
U.S. Appl. No. 12/813,882, filed Jun. 11, 2010, Ramstedt et al.
U.S. Appl. No. 12/873,708, filed Sep. 1, 2010, Ramstedt et al.
U.S. Appl. No. 12/873,704, filed Sep. 1, 2010, Ramstedt et al.
U.S. Appl. No. 12/873,705, filed Sep. 1, 2010, Ramstedt et al.
Additional data for N-(7-Oxadecyl)deoxynojirimycin, unpublished, 1 page.
Berge et al., "Pharmaceutical Salts," Journal of Pharmaceutical Sciences, Jan. 1977, 66(1):1-19.
Butters et al., "Imino sugar inhibitors for treating the lysosomal glycosphingolipidoses," Glycobiology, 2005, 15(10):43R-52R.
Chang et al., "Novel Imino Sugar Derivatives Demonstrate Potent Antiviral Activity Against Dengue Virus," Antiviral Research, May 1, 2009, 82(2):A72-A73, 178.
Chang et al., "Novel Imino Sugar Derivatives Demonstrate Potent Antiviral Activity Against Flaviviruses," Antimicrobial Agents and Chemotherapy, Apr. 2009, 53(4):1501-1508.
Courageot et al., "Alpha-Glucosidase Inhibitors Reduce Dengue Virus Production by Affecting the Initial Steps of Virion Morphogenesis in the Endoplasmic Reticulum," Journal of Virology, Jan. 2000, 74(1):564-572.
Gu et al., "Antiviral profiles of novel iminocyclitol compounds against bovine viral diarrhea virus, West Nile virus, dengue virus and hepatitis B virus," Antiviral Chemistry & Chemotherapy, Jan. 1, 2007, 18(1):49-59.
Mehta et al., "Alpha-Galactosylceramide and Novel Synthetic Glycolipids Directly Induce the Innate Host Defense Pathway and Have Direct Activity Against Hepatitis B and C Viruses," Antimicrobial Agents and Chemotherpy, Jun. 2004, 48(6):2085-2090.
Mehta et al., "Imino sugars that are less toxic but more potent as antivirals, in vitro, compared with N-n-nonyl DNJ," Antiviral Chemistry & Chemotherapy, 2002, 13:299-304.
Schul et al., "A Dengue Fever Viremia Model in Mice Shows Reduction in Viral Replication and Suppression of the Inflammatory Response after Treatment with Antiviral Drugs," Mouse Model for Dengue Antiviral Testing, JID, Mar. 1, 2007, 196:665-674.
Shresta et al., "Murine Model for Dengue Virus-Induced Lethal Disease with Increased Vascular Permeability," Journal of Virology, Oct. 2006, 80(20):10208-10217.
Who Publication, Dengue Guidelines for Diagnosis, Treatmetn, Prevention and Control,: 2009, 160 pages.
Wu et al., "Antoviral Effects of an Iminosugar Derivative on Flavivirus Infections," Journal of Virology 2002, 76(8):3596-3604.

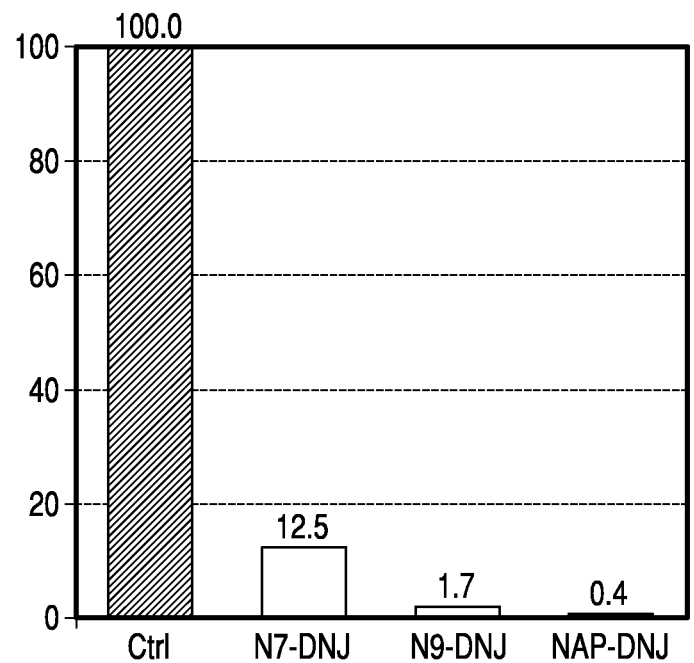

Fig. 8

| Compound | DENV IC50 uM |
|---|---|
| UV-1 | 162 |
| UV-2 | 9 |
| UV-3 | 41 |
| UV-4 | 172 |
| UV-5 | 2 |

DENV - Dengue virus

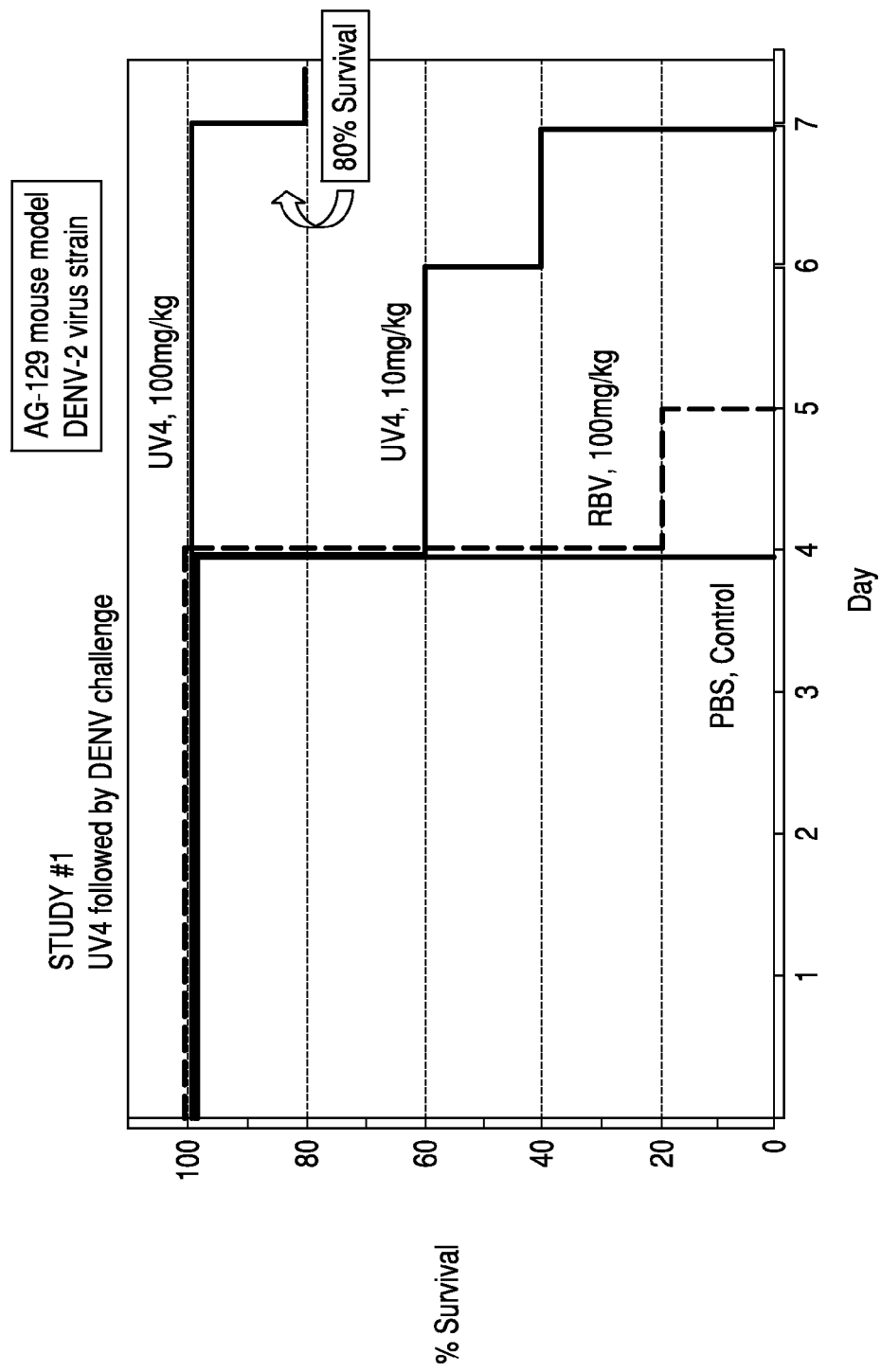

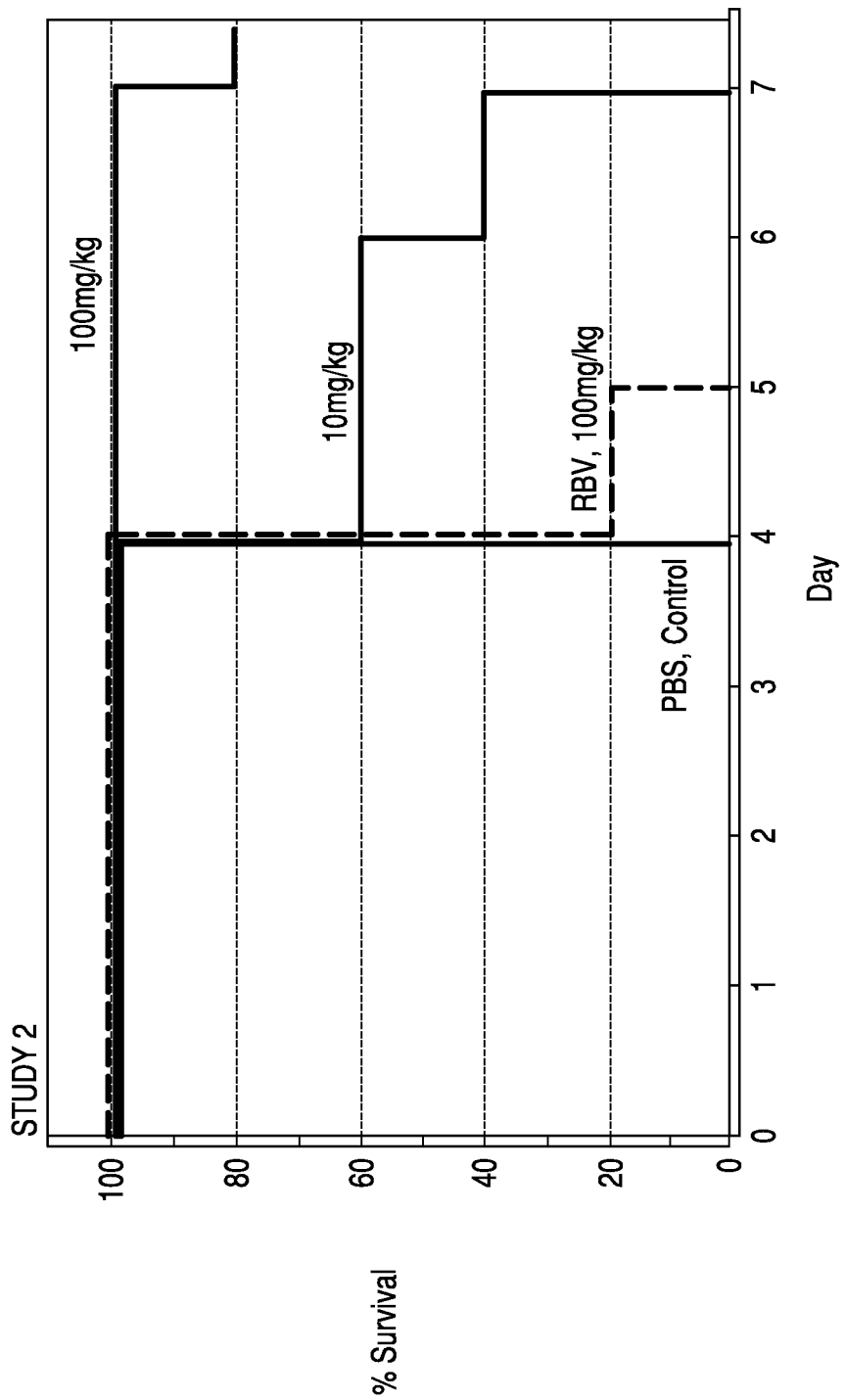

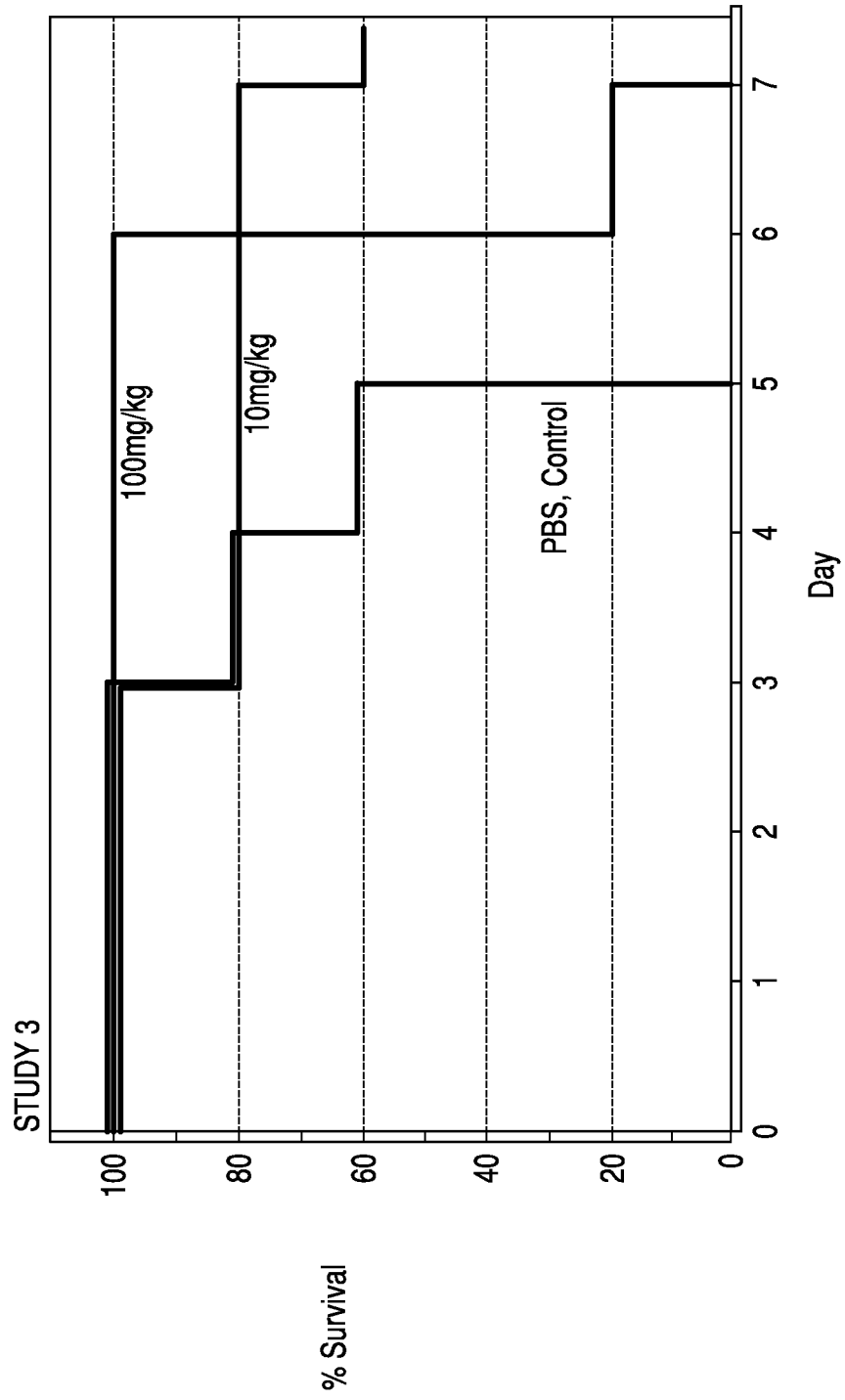

IMINOSUGARS AND METHODS OF TREATING VIRAL DISEASES

RELATED APPLICATIONS

The present application is a Continuation of U.S. application Ser. No. 12/656,992, filed Feb. 22, 2010, which claims priority to U.S. provisional applications Nos. 61/202,367 filed Feb. 23, 2009 and 61/272,255 filed Sep. 4, 2009, which are all incorporated herein by reference in their entirety.

FIELD

The present application relates to iminosugars and methods of treating or preventing viral infections with iminosugars and, in particular, to iminosugars and methods of treating or preventing viral infection associated with Dengue viruses.

SUMMARY

A method of treating or preventing a Dengue viral infection comprises administering to a subject in need thereof an effective amount of a compound of the formula,

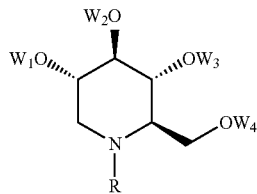

or a pharmaceutically acceptable salt thereof, wherein R is substituted or unsubstituted oxaalkyl groups; or wherein R is

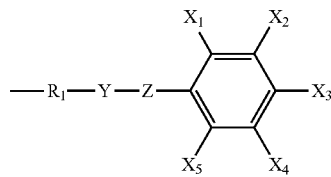

$R_1$ is an oxaalkyl group;
$X_{1-5}$ are independently selected from H, $NO_2$, $N_3$, or $NH_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl; and
wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

DRAWINGS

FIGS. 1(A)-(E) present chemical formulas of the following iminosugars: A) N-Butyl deoxynojirimycin (NB-DNJ or UV-1); B) N-Nonyl dexoynojirimycin (NN-DNJ or UV-2); C) N-(7-Oxadecyl)deoxynojirimycin (N-7-O-DNJ or N7-DNJ or UV-3); D) N-(9-Methoxynonyl)deoxynojirimycin (N-9-DNJ or UV-4); E) N—(N-{4'-azido-2'-nitrophenyl}-6-aminohexyl)deoxynojirimycin (NAP-DNJ or UV-5).

Figure 5A:
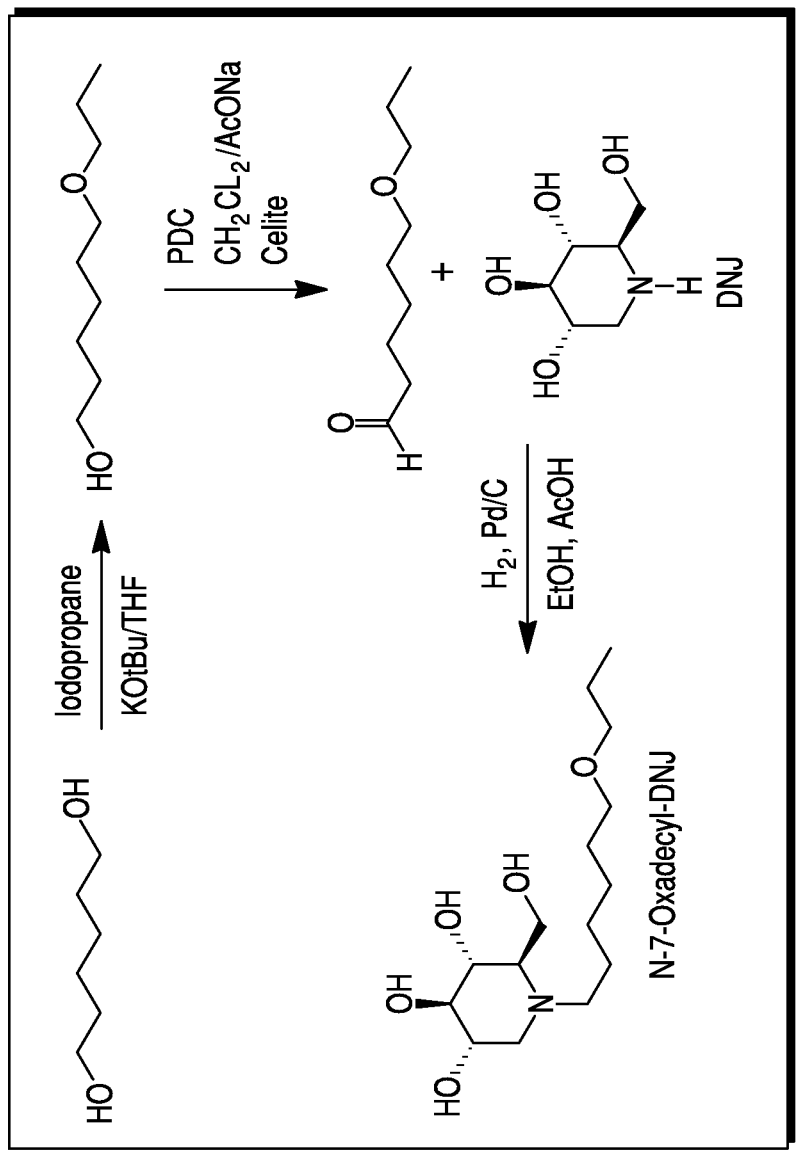
Figure 5B:
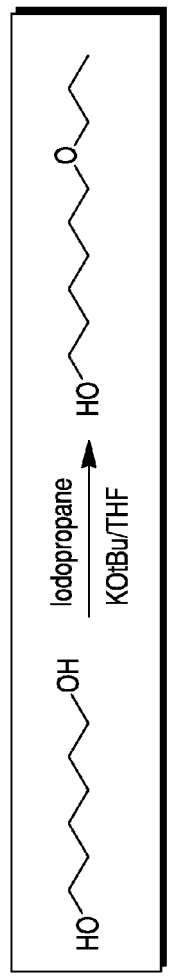
Figure 5C:
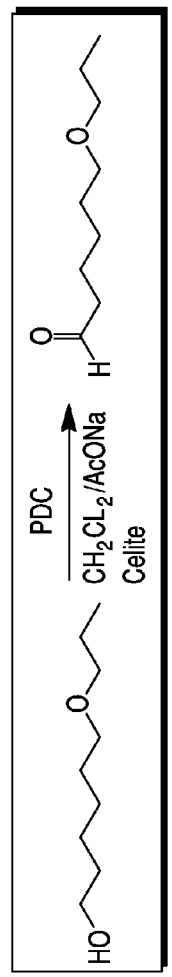
Figure 5D:
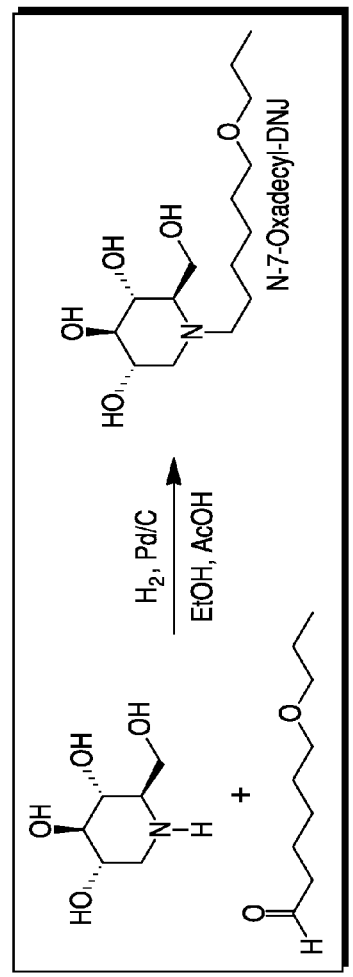

FIGS. 5A-D illustrate synthesis of N7-O-DNJ. In particular, FIG. 5A shows a sequence of reactions leading to N7-O-DNJ; FIG. 5B illustrates preparation of 6-propyloxy-1-hexanol; FIG. 5C illustrates preparation of 6-propyloxy-1-hexanal; FIG. 5D illustrates synthesis of N7-O-DNJ.

Figure 6A:
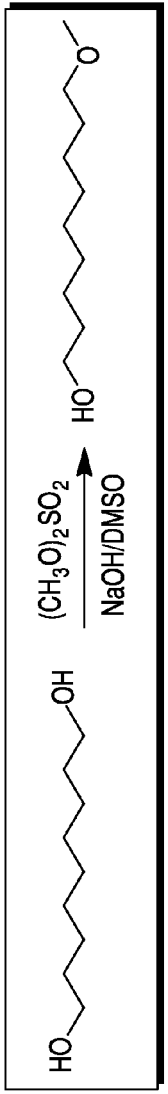
Figure 6B:
Figure 6C:
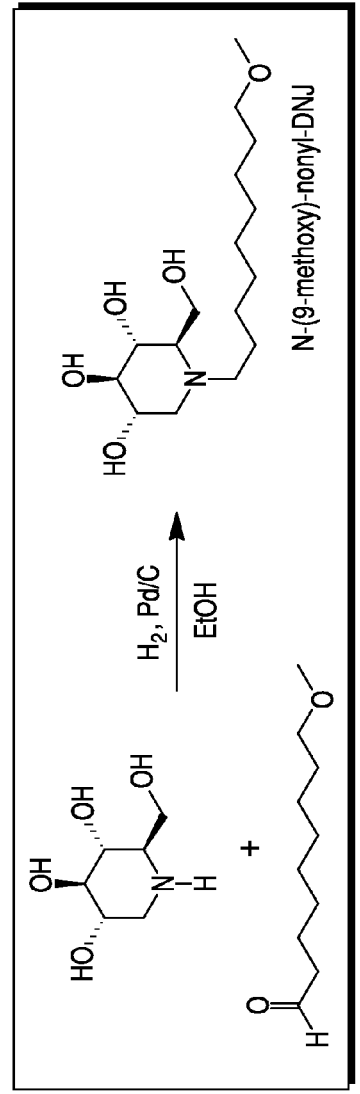

FIGS. 6A-C relate to synthesis of N-(9-Methoxynonyl) deoxynojirimycin. In particular, FIG. 6A illustrates preparation of 9-methoxy-1-nonanol; FIG. 6B illustrates preparation of 9-methoxy-1-nonanal; FIG. 6C illustrates synthesis of N-(9-Methoxynonyl)deoxynojirimycin.

FIG. 7 presents data on the inhibition of dengue virus release by N7-O-DNJ; N9-DNJ and NAP-DNJ.

FIG. 8 is a table presenting IC50 values against Dengue virus for NB-DNJ (UV-1), NN-DNJ (UV-2), N7-O-DNJ (UV-3), N9-DNJ (UV-4) and NAP-DNJ (UV-5).

Figure 9:
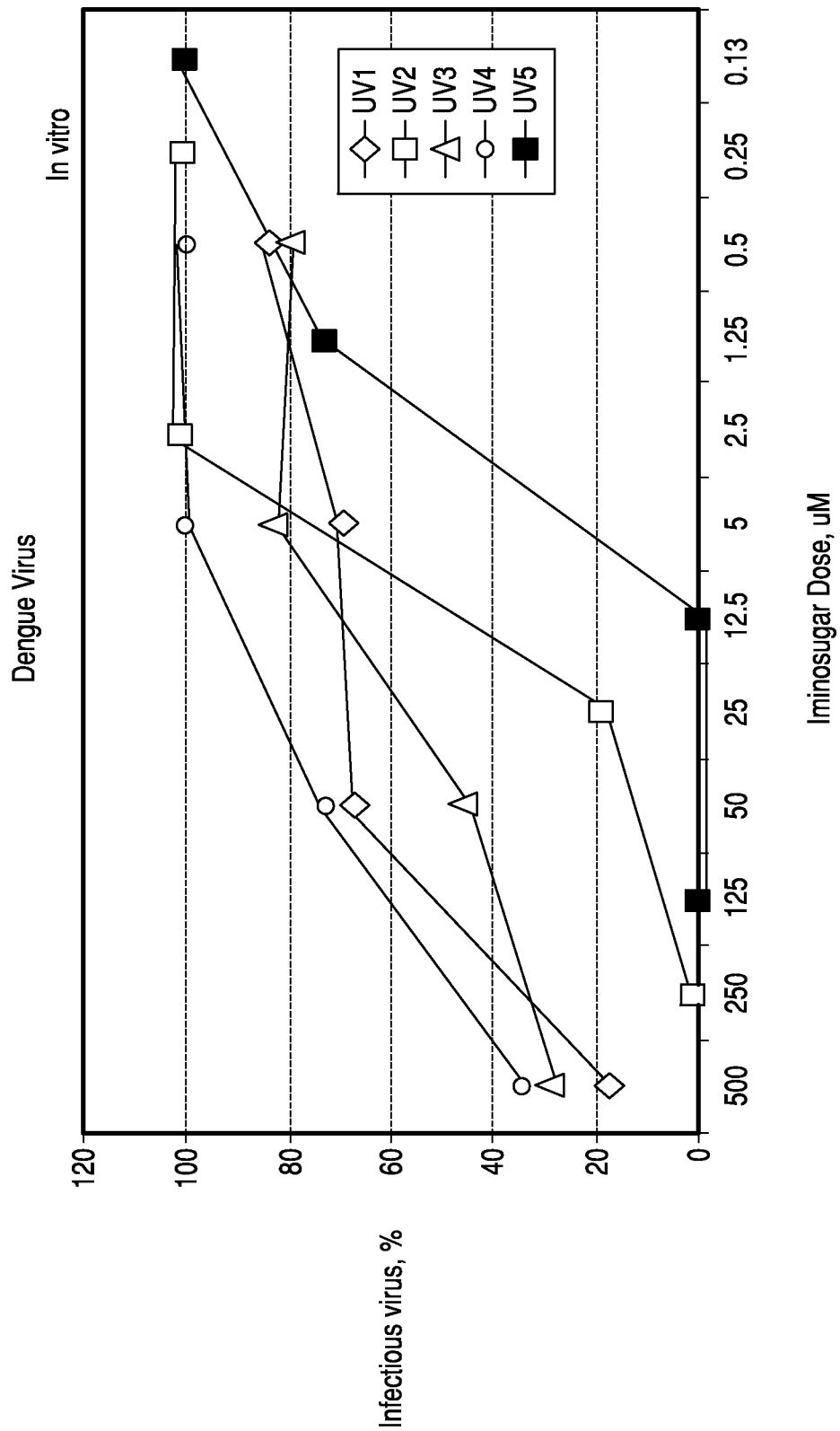

FIG. 9 presents data on the inhibition of dengue virus release by the following UV iminosugar compounds: NB-DNJ (UV-1); NN-DNJ (UV-2); N7-O-DNJ (UV-3); N9-DNJ (UV-4); NAP-DNJ (UV-5).

FIG. 10 shows protection of mice against Dengue virus by UV-4 (N-9-DNJ).

Figure 11C:
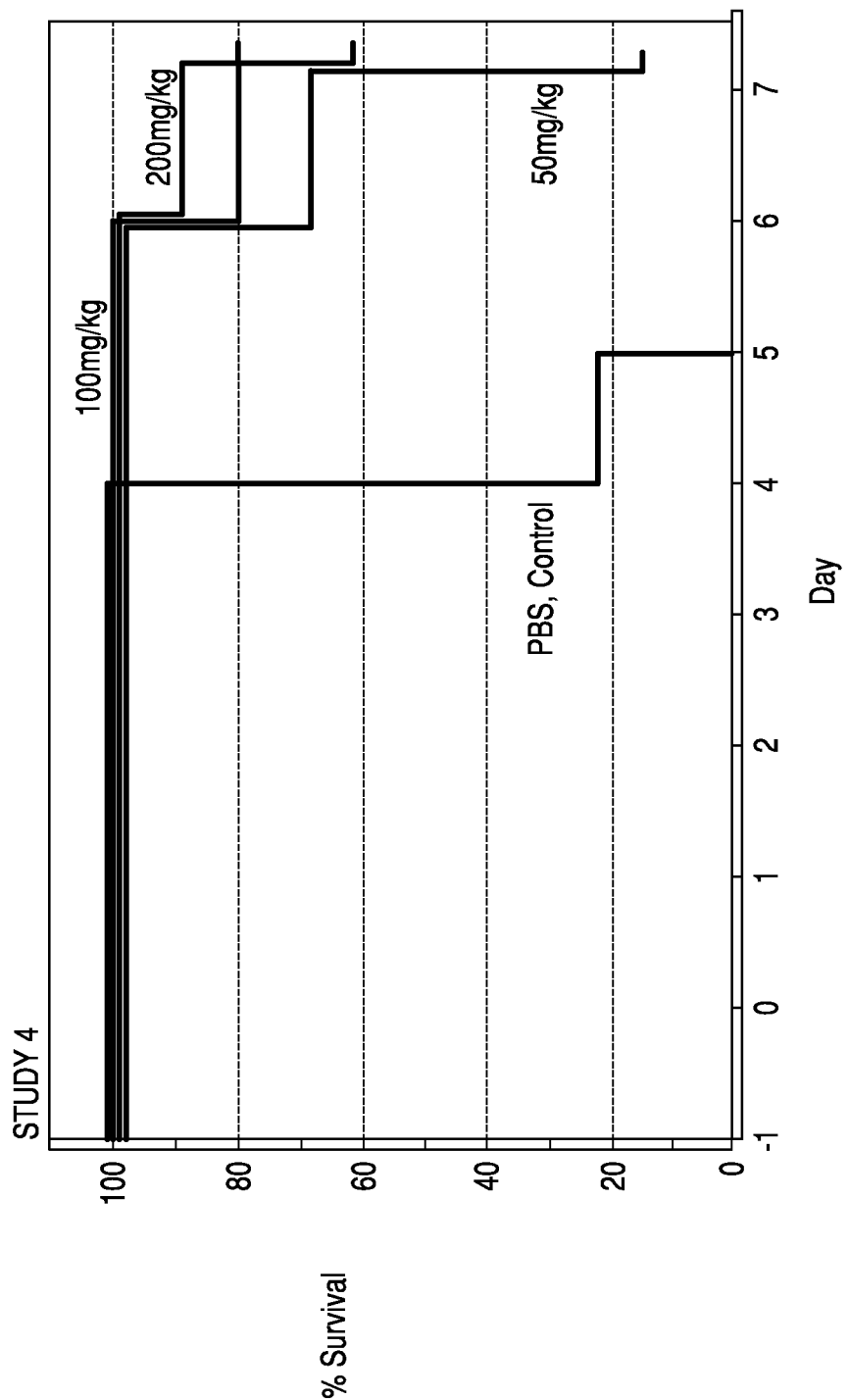

FIGS. 11A-C relate to protection of mice against Dengue virus by UV-4 (N-9-DNJ).

DETAILED DESCRIPTION

Definition of Terms

Unless otherwise specified, "a" or "an" means "one or more."

As used herein, the term "viral infection" describes a diseased state, in which a virus invades a healthy cell, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating or preventing viral infection" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

IC50 or IC90 (inhibitory concentration 50 or 90) is a concentration of a therapeutic agent, such as an iminosugar, used to achieve 50% or 90% reduction of viral infection, respectively.

RELATED APPLICATIONS

The present application incorporates by reference in its entirety U.S. provisional application No. 61/202,367 filed Feb. 23, 2009.

DISCLOSURE

The present inventors discovered that certain iminosugars, such as deoxynojirimycin derivatives, may be effective against a Dengue 1-4 virus.

In particular, the iminosugars may be useful for treating or preventing a disease or condition caused by or associated with a Dengue 1-4 virus. In some embodiments, the iminosugars may increase a survival rate or probability for a subject infected with a Dengue virus.

Dengue Viruses

Dengue virus belongs to the genus *Flavivirus* of the Flaviridae family and causes dengue hemorrhagic fever (DHF). Dengue virus includes four closely related serotypes, usually referred to as Dengue 1, Dengue 2, Dengue 3 and Dengue 4. Recovery from infection by one provides lifelong immunity against that serotype but confers only partial and transient protection against infection by the other three. A good evidence exists that sequential infection increases the risk of more serious disease, resulting in DHF. Emerging DHF epidemics are causing increasing concern in the Americas and in Asia, where all four dengue viruses are endemic. DHF has become a leading cause of hospitalization and death among children in several countries. In 2007, there were more than 890,000 reported cases of dengue in the Americas, of which 26,000 cases were DHF.

Dengue is transmitted primarily by the *Aedes aegypti* mosquito and is the most common mosquito-borne viral disease of humans. Globally, 2.5 billion people—40% of the world's population—live in the warm areas where *Aedes aegypti* is common and dengue can be transmitted. The rapid growth of tropical cities and their human and mosquito populations is bringing ever greater numbers of people into contact with this vector. The geographical spread of both the mosquito vectors and the virus has led to a global resurgence of epidemic dengue fever and the emergence of dengue hemorrhagic fever (DHF).

Iminosugars

In many embodiments, the iminosugar may be N-substituted deoxynojirimycin. In some embodiments, as the N-substituted deoxynojirimycin may be a compound of the following formula:

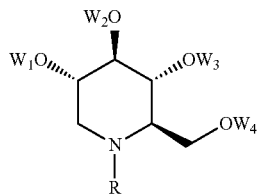

where $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups.

In some embodiments, R may be selected from substituted or unsubstituted alkyl groups, substituted or unsubstituted cycloalkyl groups, substituted or unsubstituted aryl groups, or substituted or unsubstituted oxaalkyl groups.

In some embodiments, R may be substituted or unsubstituted alkyl groups and/or substituted or unsubstituted oxaalkyl groups comprise from 1 to 16 carbon atoms, from 4 to 12 carbon atoms or from 8 to 10 carbon atoms. The term "oxaalkyl" refers to an alkyl derivative, which may contain from 1 to 5 or from 1 to 3 or from 1 to 2 oxygen atoms. The term "oxaalkyl" includes hydroxyterminated and methoxyterminated alkyl derivatives.

In some embodiments, R may be selected from, but is not limited to —(CH$_2$)$_6$OCH$_3$, —(CH$_2$)$_6$OCH$_2$CH$_3$, —(CH$_2$)$_6$O (CH$_2$)$_2$CH$_3$, —(CH$_2$)$_6$O(CH$_2$)$_3$CH$_3$, —(CH$_2$)$_2$O(CH$_2$)$_5$CH$_3$, —(CH$_2$)$_2$O(CH$_2$)$_6$CH$_3$; —(CH$_2$)$_2$O(CH$_2$)$_7$CH$_3$; —(CH$_2$)$_9$—OH; —(CH$_2$)$_9$OCH$_3$.

In some embodiments, R may be an branched or unbranched, substituted or unsubstituted alkyl group. In certain embodiments, the alkyl group may be a long chain alkyl group, which may be C6-C20 alkyl group; C8-C16 alkyl group; or C8-C10 alkyl group. In some embodiments, R may be a long chain oxaalkyl group, i.e. a long chain alkyl group, which may contain from 1 to 5 or from 1 to 3 or from 1 to 2 oxygen atoms.

In some embodiments, R may have the following formula

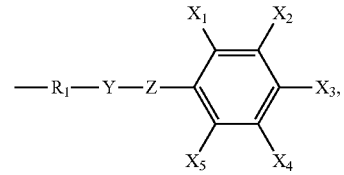

where $R_1$ is a substituted or unsubstituted alkyl group;
$X_{1-5}$ are independently selected from H, NO$_2$, N$_3$, or NH$_2$;
Y is absent or is a substituted or unsubstituted $C_1$-alkyl group, other than carbonyl; and
Z is selected from a bond or NH; provided that when Z is a bond, Y is absent, and provided that when Z is NH, Y is a substituted or unsubstituted $C_1$-alkyl group, other than carbonyl.

In some embodiments, Z is NH and $R_1$—Y is a substituted or unsubstituted alkyl group, such as C2-C20 alkyl group or C4-C12 alkyl group or C4-C10 alkyl group.

In some embodiments, $X_1$ is NO$_2$ and $X_3$ is N$_3$. In some embodiments, each of $X_2$, $X_4$ and $X_5$ is hydrogen.

In some embodiments, the iminosugar may be a DNJ derivative disclosed in U.S. patent application publication no. 2007/0275998, which is incorporated herein by reference.

In some embodiments, the iminosugar may be one of the compounds presented in FIG. 1. Iminosugars, such as deoxynojirimycin derivatives, may be synthesized as disclosed, for example, in U.S. Pat. Nos. 5,622,972, 5,200,523, 5,043, 273, 4,994,572, 4,246,345, 4,266,025, 4,405,714, and 4,806, 650 and U.S. patent application publication no. US2007/ 0275998, which are all incorporated herein in their entirety.

In some embodiments, the iminosugar may be in a form of a salt derived from an inorganic or organic acid. Pharmaceutically acceptable salts and methods for preparing salt forms are disclosed, for example, in Berge et al. (*J. Pharm. Sci.* 66:1-18, 1977). Examples of appropriate salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

In some embodiments, the iminosugar may also used in a form of a prodrug. Prodrug of DNJ derivatives, such as the 6-phosphorylated DNJ derivatives, are disclosed in U.S. Pat. Nos. 5,043,273 and 5,103,008.

In some embodiments, the iminosugar may be used as a part of a composition, which further comprises a pharmaceutically acceptable carrier and/or a component useful for delivering the composition to an animal. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

In some embodiments, the pharmaceutical composition may consist essentially of iminosugar, which may mean that the iminosugar is the only active ingredient in the composition.

Yet in some embodiments, the iminosugar may be administered with one or more additional antiviral compounds.

In some embodiments, the iminosugar may be used in a liposome composition, such as those disclosed in US publication 2008/0138351; U.S. application Ser. No. 12/410,750 filed Mar. 25, 2009 and U.S. provisional application No. 61/202,699 filed Mar. 27, 2009.

The iminosugar may be administered to a cell or an individual affected by a virus. The iminosugar may inhibit morphogenesis of the virus, or it may treat the individual. The treatment may reduce, abate, or diminish the virus infection in the animal.

Animals that may be infected with Dengue viruses include vertebrates, such as mammals, including rodents and primates, including humans.

The amount of iminosugar administered to an animal or to an animal cell to the methods of the invention may be an amount effective to inhibit the morphogenesis of Dengue virus from the cell. The term "inhibit" as used herein may refer to the detectable reduction and/or elimination of a biological activity exhibited in the absence of the iminosugar. The term "effective amount" may refer to that amount of the iminosugar necessary to achieve the indicated effect. The term "treatment" as used herein may refer to reducing or alleviating symptoms in a subject, preventing symptoms from worsening or progressing, inhibition or elimination of the causative agent, or prevention of the infection or disorder related to the Dengue virus in a subject who is free therefrom.

Thus, for example, treatment of the infection caused or associated with Dengue virus may include destruction of the infecting agent, inhibition of or interference with its growth or maturation, and neutralization of its pathological effects. The amount of the iminosugar which may be administered to the cell or animal is preferably an amount that does not induce any toxic effects which outweigh the advantages which accompany its administration.

Actual dosage levels of active ingredients in the pharmaceutical compositions may vary so as to administer an amount of the active compound(s) that is effective to achieve the desired therapeutic response for a particular patient.

The selected dose level may depend on the activity of the iminosugar, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated. The adult human daily dosage may range from between about one microgram to about one gram, or from between about 10 mg and 100 mg, of the iminosugar per 10 kilogram body weight. Of course, the amount of the iminosugar which should be administered to a cell or animal may depend upon numerous factors well understood by one of skill in the art, such as the molecular weight of the iminosugar and the route of administration.

Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the iminosugar, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the iminosugar. Such pharmaceutical compositions may be administered by a number of routes. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered in a single dose or in multiple doses which are administered at different times. Because the inhibitory effect of the composition upon the Dengue virus may persist, the dosing regimen may be adjusted such that virus propagation is retarded while the host cell is minimally effected. By way of example, an animal may be administered a dose of the composition of the invention once per week, whereby virus propagation is retarded for the entire week, while host cell functions are inhibited only for a short period once per week.

Embodiments described herein are further illustrated by, though in no way limited to, the following working examples.

Working Examples

1. Synthesis of N-Nonyl DNJ

TABLE 1

Materials for NN-DNJ synthesis

| Name | Amount |
|---|---|
| DNJ | 500 mg |
| Nonanal | 530 mg |
| Ethanol | 100 mL |
| AcOH | 0.5 mL |
| Pd/C | 500 mg |

Procedure: A 50-mL, one-necked, round-bottom flask equipped with a magnetic stirrer was charged with DNJ (500 mg), ethanol (100 mL), nonanal (530 mg), and acetic acid (0.5 mL) at room temperature. The reaction mixture was heated to 40-45° C. and stirred for 30-40 minutes under nitrogen. The reaction mixture was cooled to ambient temperature and Pd/C was added. The reaction flask was evacuated and replaced by hydrogen gas in a balloon. This process was repeated three times. Finally, the reaction mixture was stirred at ambient temperature overnight. The progress of reaction was monitored by TLC (Note 1). The reaction mixture was filtered through a pad of Celite and washed with ethanol. The filtrate was concentrated in vacuo to get the crude product. The crude product was purified by column chromatography (230-400 mesh silica gel). A solvent gradient of methanol in dichloromethane (10-25%) was used to elute the product from the column. All fractions containing the desired product were combined, and concentrated in vacuo to give the pure product (420 mg). Completion of the reaction was monitored by thin layer chromatography (TLC) using a thin layer silica gel plate; eluent; methanol:dichloromethane=1:2

2. Synthesis of N-7-Oxadecyl DNJ

2a. Synthesis of 6-propyloxy-1-hexanol

TABLE 2

| Materials for synthesis of 6-propyloxy-1-hexanol | |
|---|---|
| Name | Amount |
| 1,6-hexanediol | 6.00 g |
| 1-Iodopropane | 8.63 g |
| Potassium tert-butoxide | 5.413 mg |
| THF | 140 mL |

Procedure: a 500-mL, one-necked, round-bottom flask equipped with a magnetic stirrer was charged with 1,6-hexanediol (6.00 g), potassium tert-butoxide (5.413 g) at room temperature. The reaction mixture was stirred for one hour, and then 1-iodopropane (8.63 g) was added. The reaction mixture was heated to 70-80° C. and stirred overnight. The progress of reaction was monitored by TLC (Note 1). After completion of the reaction, water was added to the reaction mixture, and extracted with ethyl acetate (2×100 mL). The combined organic layers were concentrated in vacuo to get the crude product. The crude product was dissolved in dichloromethane and washed with water, and then brine, dried over sodium sulfate. The organic layer was concentrated in vacuo to get the crude product. The crude product was purified by column chromatography using 230-400 mesh silica gel. A solvent gradient of ethyl acetate in hexanes (10-45%) was used to elute the product from the column. All fractions containing the desired pure product were combined and concentrated in vacuo to give pure 6-propyloxy-1-hexanol (lot D-1029-048, 1.9 g, 25%) Completion of the reaction was monitored by thin layer chromatography (TLC); (eluent: 60% ethyl acetate in hexanes).

2b. Preparation of 6-propyloxy-1-hexanal

TABLE 3

| Materials for preparation of 6-propyloxy-1-hexanal | |
|---|---|
| Name | Amount |
| 6-Propyloxy-1-hexanol | 1.00 g |
| PDC | 4.70 g |
| Celite | 1.00 g |
| NaOAc | 100 mg |
| $CH_2Cl_2$ | 10 mL |

Procedure: a 50-mL, one-necked, round-bottom flask equipped with a magnetic stirrer was charged with 6-propyloxy-1-hexanol (1.0 g), PDC (4.7 g), dichloromethane (10 mL), Celite (1.0 g), and sodium acetate (100 mg). The reaction mixture was stirred at room temperature under nitrogen for 5 minutes. PDC (4.70 g) was added to the reaction mixture, and stirred overnight. The progress of reaction was monitored by TLC (Note 1). After completion of the reaction, the reaction mixture was directly loaded on the column (230-400 mesh silica gel). A solvent gradient of dichloromethane in ethyl acetate (10-20%) was used to elute the product from the column. All fractions containing the desired pure product were combined and concentrated in vacuo to give pure 6-propyloxy-1-hexanal (lot D-1029-050, 710 mg, 71%). Completion of the reaction was monitored by thin layer chromatography (TLC); (eluent: 60% ethyl acetate in hexanes).

2c Synthesis of N-7-Oxadecyl-DNJ

TABLE 4

| Materials for Synthesis of N-7-Oxadecyl-DNJ | |
|---|---|
| Name | Amount |
| DNJ | 500 mg |
| 6-Propyloxy-1-hexanal | 585 mg |
| Pd/C | 125 mg |
| Ethanol | 15 mL |
| Acetic acid | mL |

Procedure: a 50-mL, one-necked, round-bottom flask equipped with a magnetic stirrer was charged with DNJ (500 mg), ethanol (15 mL), 6-propyloxy-1-hexanal (585 mg), and acetic acid (0.1 mL) t room temperature. The reaction mixture was heated to 40-45° C. and stirred for 30-40 minutes under nitrogen. The reaction mixture was cooled to ambient temperature and Pd/C was added. The reaction flask was evacuated and replaced by hydrogen gas in a balloon. This process was repeated three times. Finally, the reaction mixture was stirred at ambient temperature overnight. The progress of reaction was monitored by TLC (Note 1). The reaction mixture was filtered through a pad of Celite and washed with ethanol. The filtrate was concentrated in vacuo to get the crude product. The crude product was purified by column chromatography (230-400 mesh silica gel). A solvent gradient of methanol in dichloromethane (10-40%) was used to elute the product from the column. All fractions containing the desired product were combined, and concentrated in vacuo to give the pure product. (Lot: D-1029-052 (840 mg). Completion of the reaction was monitored by thin layer chromatography (TLC); (eluent: 50% methanol in dichloromethane).

3. Synthesis of N-(9-methoxy)-nonyl DNJ

3a Preparation of 9-methoxy-1-nonanol

TABLE 5

| Materials for preparation of 9-methoxy-1-nonanol | |
|---|---|
| Name | Amount |
| 1,9-nonanediol | 10.0 g |
| Dimethyl sulfate | 41.39 g |
| Sodium hydroxide | 5.0 g |
| DMSO | 100 mL |

Procedure: a 500-mL, one-necked, round-bottom flask equipped with a magnetic stirrer and stir bar was charged with 1,9-nonanediol (10.00 g, 62.3 mmol) in dimethyl sulfoxide (100 mL) and $H_2O$ (100 mL). To this was added slowly a solution of sodium hydroxide (5.0 g, 125.0 mmol) in $H_2O$ (10 mL) at room temperature. During addition of sodium hydroxide the reaction mixture generated heat and the temperature rose to ~40° C. The mixture was stirred for one hour, and then dimethyl sulfate (16.52 g, 131 mmol) was added in four portions while maintaining the temperature of the reaction mixture at ~40° C. The reaction mixture was stirred at room temperature overnight. Progress of the reaction was monitored by TLC (Note 1). TLC monitoring indicated that the reaction was 25% conversion. At this stage additional dimethyl sulfate (24.78 g, 196.44 mmol) was added and the resulting mixture was stirred at room temperature for an additional 24 h. After completion of the reaction, sodium hydroxide (10% solution in water) was added to the reaction mixture to adjust the pH of the solution to 11-13. The mixture was stirred at room temperature for 2 h and extracted with dichloromethane (3×100 mL). The combined organic layers were washed with $H_2O$ (200 mL), brine (150 mL), dried over anhydrous sodium sulfate (20 g), filtered and concentrated in vacuo to obtain a crude product (14 g). The crude product was purified by column chromatography using 250-400 mesh silica gel. A solvent gradient of ethyl acetate in hexanes (10-50%) was used to elute the product from the column. All fractions containing the desired pure product were combined and concentrated in vacuo to give pure 9-methoxy-1-nonanol (lot D-1027-155, 2.38 g, 21.9%). Completion of the reaction was monitored by thin layer chromatography (TLC) using a thin layer silica gel plate; eluent: 60% ethyl acetate in hexanes.

3b Preparation of 9-methoxy-1-nonanal

TABLE 6

Materials for preparation of 9-methoxy-1-nonanal

| Name | Amount |
| --- | --- |
| 9-methoxy-1-nonanol | 1.0 g |
| PDC | 4.7 g |
| Molecular sieves, 3A | 1.0 g |
| NaOAc | 0.1 g |
| $CH_2Cl_2$ | 10 mL |

Procedure: a 50-mL, one-necked, round-bottom flask equipped with a magnetic stirrer and stir bar was charged with 9-methoxy-nonanol (1.0 g, 5.9 mmol), dichloromethane (10 mL), molecular sieves (1.0 g, 3 A), sodium acetate (0.1 g) at room temperature. The reaction mixture was stirred at room temperature under nitrogen for 5 minutes. The reaction mixture was charged with pyridinium dichromate (4.7 g, 12.5 mmol) and stirred overnight. The progress of reaction was monitored by TLC (Note 1). After completion of the reaction, the reaction mixture was filtered through a bed of silica gel (~15 g). The filtrate was evaporated in vacuo to obtain a crude compound. This was purified by column chromatography using silica gel column (250-400 mesh, 40 g). A solvent gradient of ethyl acetate in hexane (10-50%) was used to elute the product from the column. All fractions containing the desired pure product were combined and concentrated in vacuo to give pure 9-methoxy-nonanal (lot D-1027-156, 553 mg, 54.4%). Completion of the reaction was monitored by thin layer chromatography (TLC) using a thin layer silica gel plate; eluent: 60% ethyl acetate in hexanes.

3c Synthesis of N-(9-methoxy)-nonyl DNJ

TABLE 7

Materials for synthesis of N-(9-methoxy)-nonyl DNJ

| Name | Amount |
| --- | --- |
| DNJ | 300 mg |
| 9-methoxy-1-nonanal | 476 mg |
| Pd/C | 200 mg |
| Ethanol | 20 mL |

Procedure: a 50-mL, two-necked, round-bottom flask equipped with magnetic stirrer and a stir bar was charged with DNJ (300 mg, 1.84 mmol), ethanol (20 mL), 9-methoxy-1-nonanal (476 mg, 2.76 mmol) at room temperature. The reaction mixture was stirred for 5-10 minutes under nitrogen and Pd/C was added at room temperature. The reaction mixture was evacuated and was replaced by hydrogen gas using a balloon. This process was repeated three times and then reaction mixture was stirred under atmospheric hydrogen at room temperature. The progress of reaction was monitored by TLC (Note 1). The reaction mixture was filtered through a bed of Celite and was washed with ethanol (20 mL). The filtrate was concentrated in vacuo to get a crude product. The crude product was purified by column chromatography using 250-400 mesh silica gel (20 g). A solvent gradient of methanol in ethyl acetate (5-25%) was used to elute the product from the column. All fractions containing the desired pure product were combined, and concentrated in vacuo to give an off white solid. The solid was triturated in ethyl acetate (20 mL), filtered and dried in high vacuum to give a white solid [lot: D-1027-158 (165.3 mg, 28.1%). Completion of the reaction was monitored by thin layer chromatography (TLC) using a thin layer silica gel plate; eluent: 50% methanol in dichloromethane.

4. Effect of Iminosugars Against Dengue Virus

Figure 1A:
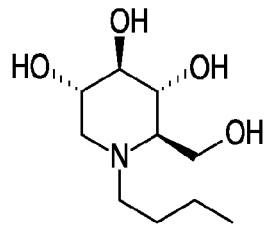
Figure 1B:
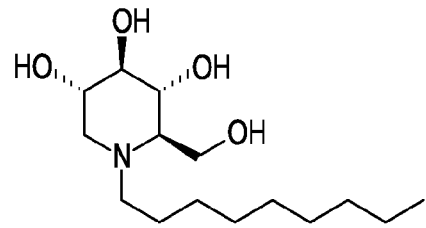
Figure 1C:
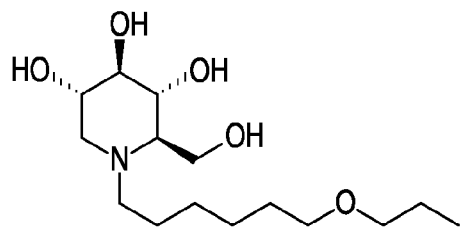
Figure 1D:
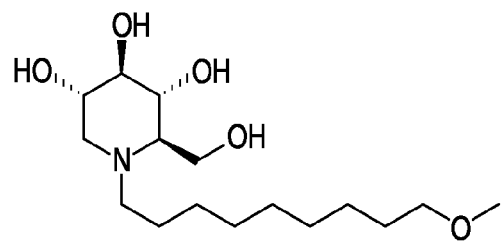
Figure 1E:
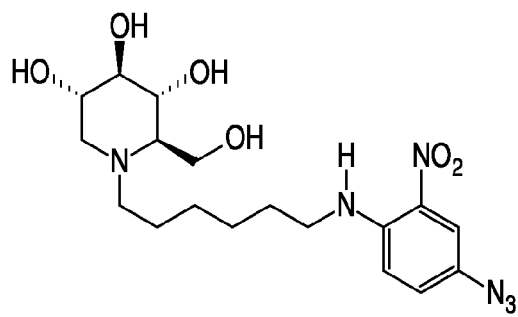
Figure 2:
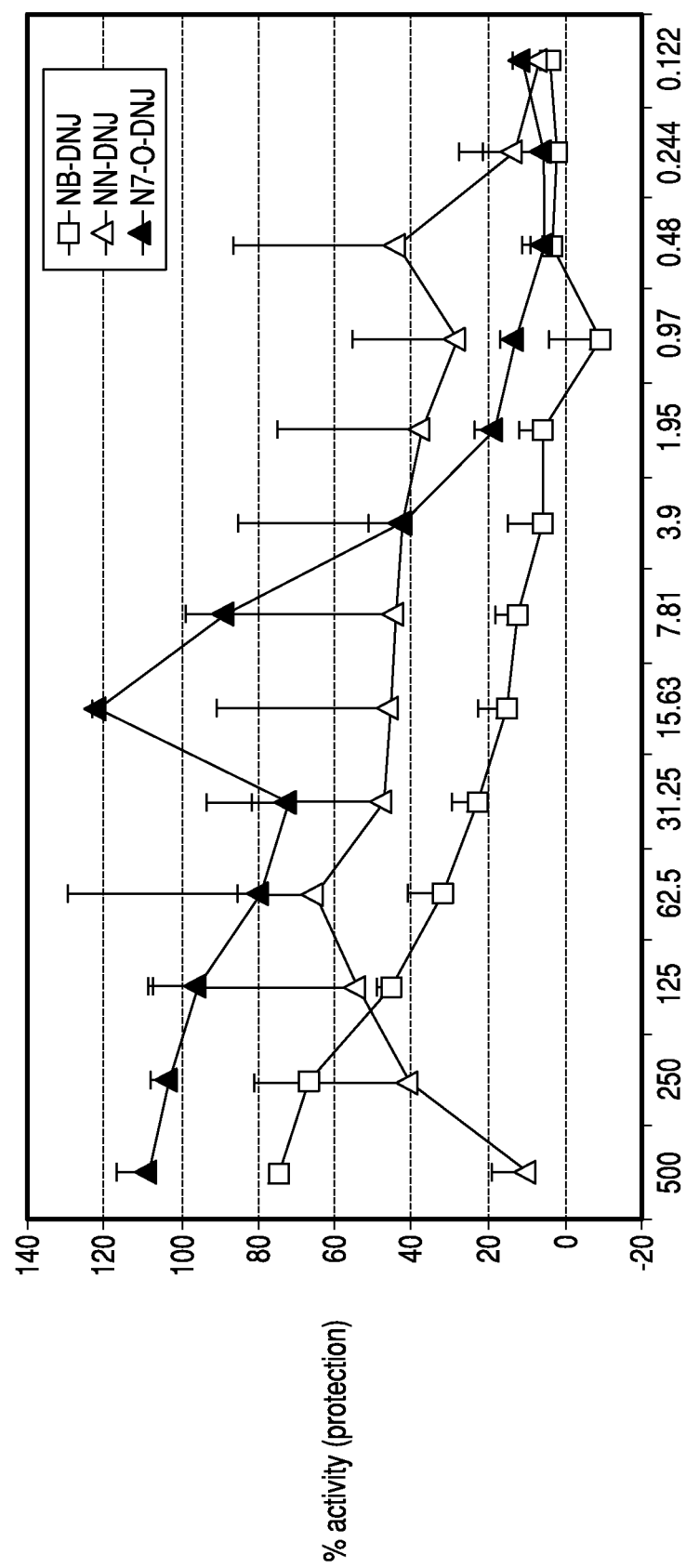
FIG. 2 is a plot presenting cell protection versus Dengue virus by NB-DNJ, NN-DNJ and N7-O-DNJ.

FIG. 2 shows cell protection against Dengue virus by NB-DNJ, NN-DNJ, and N7-O-DNJ. Procedure. Virus-induced cytopathic effect (CPE)-inhibition assay was conducted on the UV compounds at concentrations from 0.122 up to 500 uM.

The compounds were screened for inhibition against Dengue virus type 2 (DENV2), strain New Guinea C. Viral stocks were made by propagation in Vero cells using 1× modified Eagle medium (MEM, Gibco), supplemented with 2% fetal bovine serum, 2 mM L-glutamine, 100 U/ml penicillin, 100 ug/ml streptomycin and titered using the standard plaque assay. Viral stocks were stored at −80° C. until used.

Vero cells (African green monkey kidney epithelial cell line) obtained from American Type Culture Collection (ATCC, Manassas, Va.) were plated in cell culture treated 96-well flat bottom plates at 37° C. in a 5% CO2 incubator for 24 hr prior to assay. Tests were done in modified Eagle medium, supplemented with 2% fetal bovine serum, 2 mM L-glutamine, 100 U/ml penicillin, 100 ug/ml streptomycin, starting at 500 μM compounds, decreasing to 0.122 uM. On the day of assay, the media were aspirated and cells were treated with compounds at the various concentrations. After 1 hr of drug pretreatment at 37° C., Dengue virus was added to the cells with low multiplicities of infection (MOI). At 1 hr following the infection, the cells were washed and media containing compounds were added. The assay was allowed to develop for 6 days at 37° C. in a 5% CO2 incubator during which untreated, viral-infected control wells showed CPE. After the post infection period, culture supernatants were removed from the plates and assayed by LDH assay (Cyto-Tox96, Promega, WI) according to the manufacturer's recommendations for viral induced cellular damage (release of cytoplasmic enzyme lactate dehydrogenase). OD readings were used to calculate and compare percent cytopathic effect of cells treated with compounds or controls. The experiment demonstrates that the UV compounds are effective in protecting cells from killing by dengue virus, in a dose-dependent manner.

Figure 3:
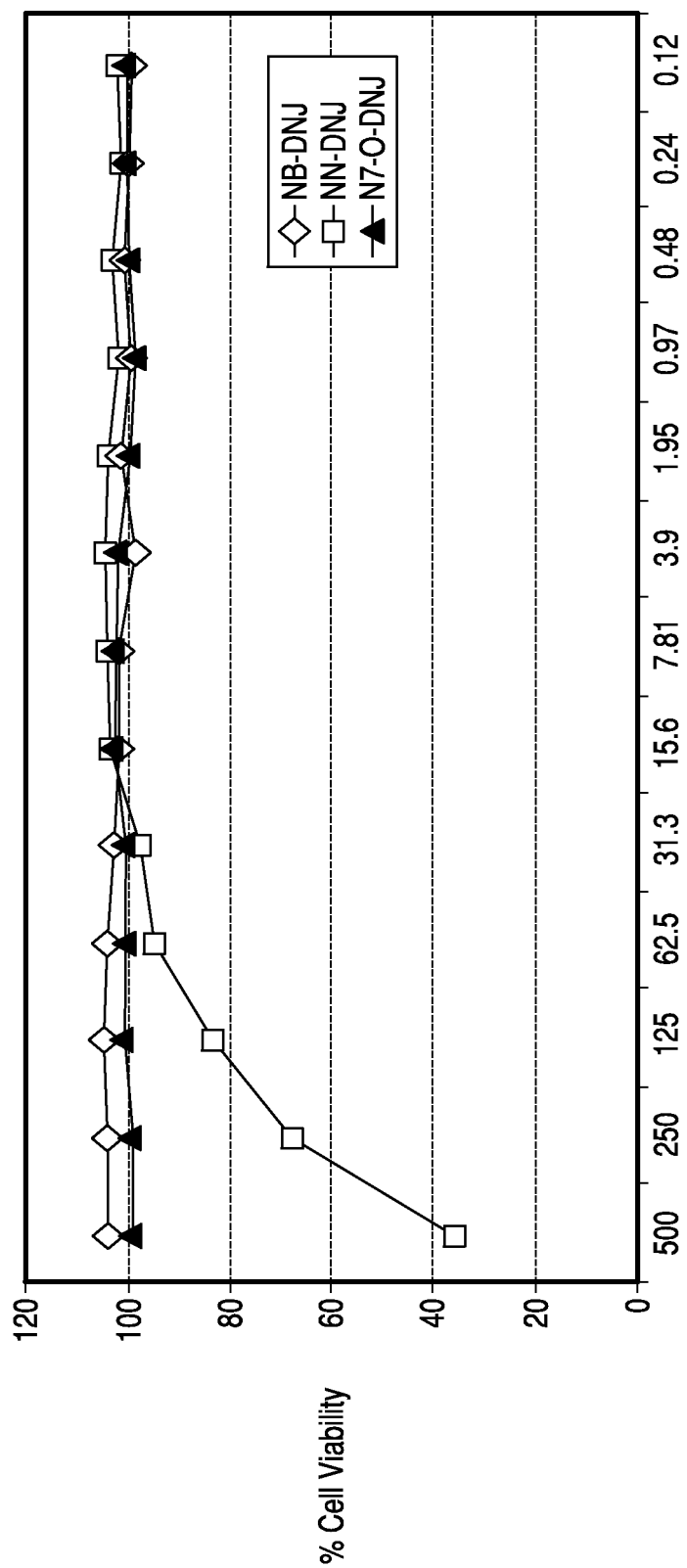
FIG. 3 is a plot of cell toxicity of NB-DNJ, NN-DNJ and N7-O-DNJ.
Figure 4:
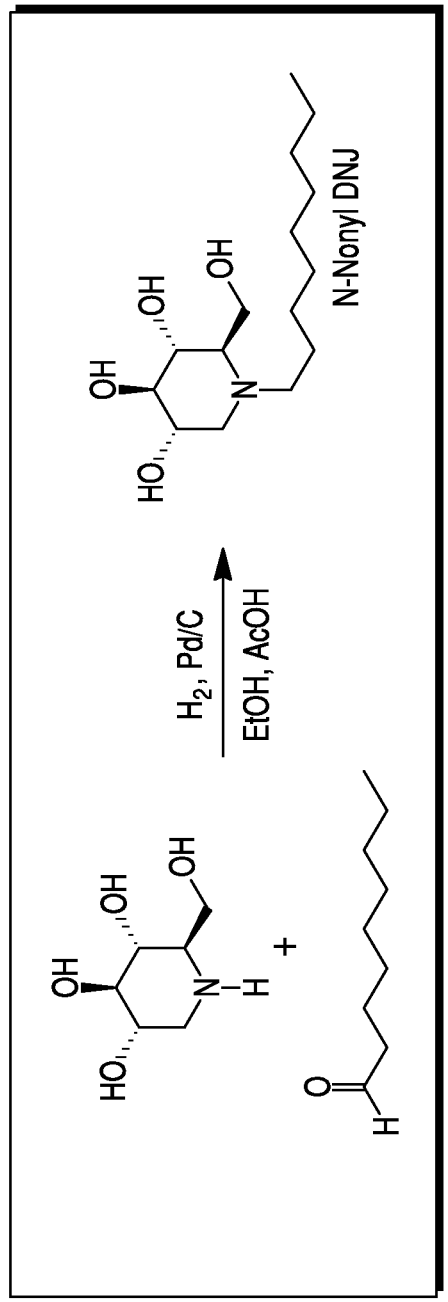
FIG. 4 is a synthesis scheme for NN-DNJ.

FIG. 3 presents cell toxicity data for NB-DNJ, NN-DNJ, and N7-O-DNJ.

Procedure. NB-DNJ, NN-DNJ and N7-O-DNJ at concentrations from 0.122 up to 500 uM were tested for cytotoxicity towards Vero cells. Vero cells (Afrika green monkey kidney epithelial cell line) obtained from American Type Culture Collection (ATCC, Manassas, Va.) were plated in cell culture treated 96-well flat bottom plates 24 hr prior to assay. Test were done in modified Eagle medium, supplemented with 2% fetal bovine serum, 2 mM L-glutamine, 100 U/ml penicillin, 100 ug/ml streptomycin, starting at 500 μM compounds, decreasing to 0.122 uM. Cells were cultured at 37° C., 5% CO2 incubator and the plates were assayed by LDH assay (CytoTox96, Promega, WI) according to the manufacturer's recommendations for induced cellular damage (release of cytoplasmic enzyme lactate dehydrogenase). OD readings were used to calculate and compare percent cytopathic effect of cells treated with compounds or controls. The experiment demonstrates that N7-O-DNJ and NB-DNJ are non-toxic to the Vero cells. NN-DNJ begins to show toxicity to the cells at concentrations above ~20 uM.

FIG. 7 presents data on the inhibition of dengue virus release by N7-O-DNJ; N9-DNJ and NAP-DNJ.

Procedure. Control Vero cell cultures and Vero cell cultures treated with 100 uM compounds were infected with virus and cultured for 7 days at 37° C. in a 5% CO2 incubator Inhibition of production of infectious virus particles from virus infected cell cultures treated with compounds were determined by plaque assay.

The virus plaque assay was performed in Vero cells plated in 6-well plates at 5×105 cells per well in 1× modified Eagle medium (Gibco), supplemented with 2% fetal bovine serum, 2 mM L-glutamine, 100 U/ml penicillin, 100 ug/ml streptomycin. The virus to be titered from collected supernatants from infected cell cultures treated with the compounds were diluted in cell culture medium and inoculated in 100 μl volumes onto cells and allowed to adsorb for 1 hr at 37° C. The cells were overlaid with 0.6% agarose in 1× modified Eagle medium (Gibco), supplemented with 2 mM Lglutamine, 100 U/ml penicillin, 100 ug/ml streptomycin. Plaques, of dead cells representing individual infectious virus particles that has infected and killed cells, were allowed to develop at 37° C. in a 5% CO2 incubator and visualized by live-staining the cell monolayer with neutral red. The experiment demonstrates that release of infectious dengue virus is significantly reduced after treatment with UV iminosugar compounds.

FIG. 9 presents data on the inhibition of dengue virus release by the following UV iminosugar compounds: NB-DNJ (UV-1); NN-DNJ (UV-2); N7-O-DNJ (UV-3); N9-DNJ (UV-4); NAP-DNJ (UV-5). Control Vero cell cultures and Vero cell cultures treated with the UV compounds at the concentrations shown were infected with virus and cultured for 7 days at 37° C. in a 5% CO2 incubator. Inhibition of production of infectious virus particles from virus infected cell cultures treated with compounds were determined by plaque assay. The virus plaque assay was performed in Vero cells plated in 6-well plates at 5×105 cells per well in 1× modified Eagle medium (Gibco), supplemented with 2% fetal bovine serum, 2 mM L-glutamine, 100 U/ml penicillin, 100 ug/ml streptomycin. The virus to be titered from collected supernatants from infected cell cultures treated with the compounds were diluted in cell culture medium and inoculated in 100 μl volumes onto cells and allowed to adsorb for 1 hr at 37° C. The cells were overlaid with 0.6% agarose in 1× modified Eagle medium (Gibco), supplemented with 2 mM L-glutamine, 100 U/ml penicillin, 100 ug/ml streptomycin. Plaques, of dead cells representing individual infectious virus particles that has infected and killed cells, were allowed to develop at 37° C. in a 5% CO2 incubator and visualized by live-staining the cell monolayer with neutral red. The experiment demonstrates that release of infectious dengue virus is significantly reduced after treatment with UV iminosugar compounds.

FIGS. 10 and 11A-C show protection of mice against Dengue virus by UV-4 (N-9-DNJ). In this model, AG129 mice, which are 129/Sv mice lacking receptors for both alpha/beta interferon and IFN-gamma, are infected with Dengue 2 strain 5221 via intravenous injection. The mice die of TNF-a mediated acute/early death 4-5 days after infection, see Shresta, S., et al., J Virol, 2006. 80(20): p. 10208-17. Each experiment group contained 5 mice sex matched and 5-6 weeks old. The mice were injected intravenously via the tail vein with $10^{11}$ genomic equivalents of DENV2 strain S221 30 min after the first N9-DNJ dose was administered orally. The N9-DNJ was administered orally twice daily at 200, 100, 50 and 10 mg/kg. The antiviral compound Ribavirin 100 mg/kg was given subcutaneously once daily and included as a positive control together with a PBS-only group. Animals displaying severe illness during the experiment (as determined by 20% weight loss, extreme lethargy, ruffled coat, or paralysis) were euthanized. Mice exhibited statistically significant improvement in survival at all drug concentrations: 100 mg/kg (p=0.002 vs. PBS) and 10 mg/kg (p=0.034 vs. PBS).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of treating Dengue viral infection comprising administering to a subject in need thereof an effective amount of the compound, where in the compound is N-(7-oxadecyl) deoxynojirimycin or a pharmaceutically acceptable salt thereof, or N—(N-{4'-azido-2 nitrophenyl}-6-aminohexyl) deoxynojirimycin or a pharmaceutically acceptable salt thereof.

2. The method of claim 1, wherein the compound is N-(7-oxadecyl)deoxynojirimycin or a pharmaceutically acceptable salt thereof.

3. The method of claim 1, wherein the compound is N—(N-{4'-azido-2'-nitrophenyl}-6-aminohexyl)deoxynojirimycin or a pharmaceutically acceptable salt thereof.

4. The method of claim 1, wherein the viral infection is caused by or associated with a Dengue 2 virus.

5. The method of claim 1, wherein the subject is a mammal.

6. The method of claim 1, wherein the subject is a human being.

* * * * *